United States Patent [19]

König et al.

[11] Patent Number: 5,364,887

[45] Date of Patent: Nov. 15, 1994

[54] PROCESS OF PRODUCING METHANOL

[75] Inventors: Peter König, Frankfurt; Friedrich-Wilhelm Möller, Friedrichsdorf; Emil Supp, Dietzenbach, all of Germany

[73] Assignee: Metallgesellschaft Aktiengesellschaft, Frankfurt am Main, Germany

[21] Appl. No.: 143,807

[22] Filed: Oct. 27, 1993

[30] Foreign Application Priority Data

Nov. 27, 1992 [DE] Germany .............................. 4239904

[51] Int. Cl.$^5$ .............................................. C07C 27/06
[52] U.S. Cl. .................................... 518/713; 518/728
[58] Field of Search ................................ 518/713, 728

[56] References Cited

U.S. PATENT DOCUMENTS 3,920,717 11/1975 Marion .
3,962,300 6/1976 Hiller et al. .
4,348,486 9/1982 Calvin et al. .

OTHER PUBLICATIONS

Ullmann's Encyclopedia of Industrial Chemistry, vol. A 16, pp. 469–475.

*Primary Examiner*—Howard T. Mars
*Attorney, Agent, or Firm*—Sprung Horn Kramer & Woods

[57] ABSTRACT

Methanol is catalytically produced from a synthesis gas which contains $H_2$, CO and $CO_2$ in a synthesis reactor at temperatures from 220° to 300° C. and under a pressure in the range from 20 to 120 bars. A product mixture which contains methyl formate is withdrawn from the synthesis reactor and is cooled to temperatures in the range from 20° to 60° to provide a condensate which contains methanol, water and methylformate. A gas mixture which contains $H_2$, CO and $CO_2$ is formed at the same time. A fraction which comprises 10 to 100% by weight methyl formate is separated from the condensate and is admixed with the synthesis gas which is fed to the synthesis reactor.

6 Claims, 1 Drawing Sheet

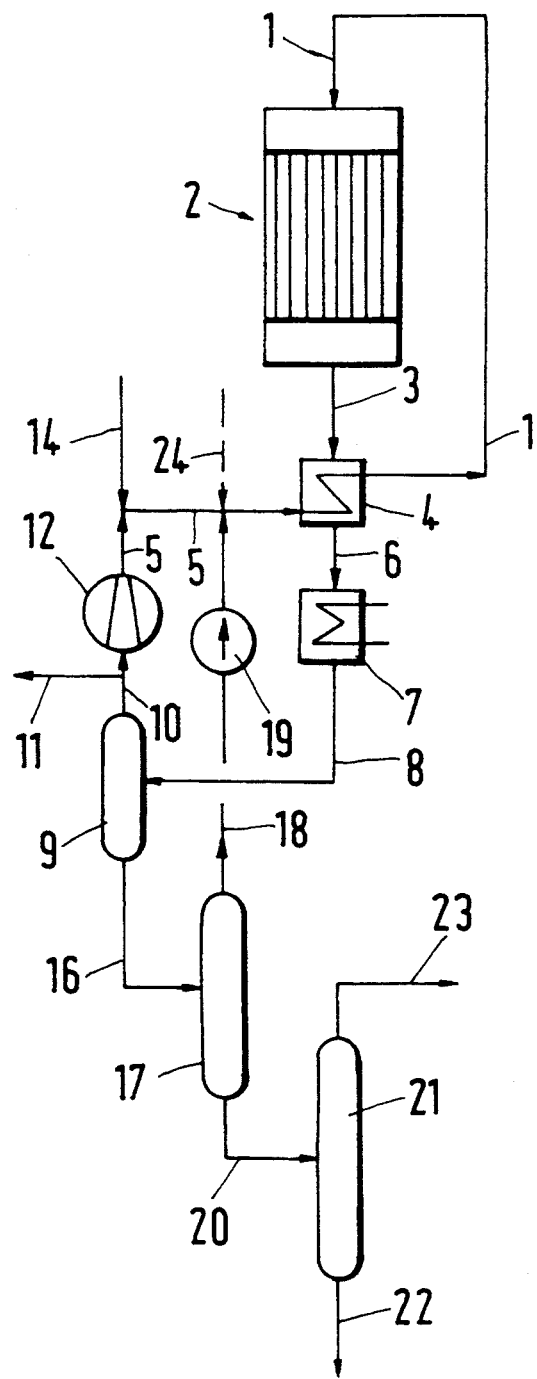

PROCESS OF PRODUCING METHANOL

This invention relates to a process for the catalytic production of methanol from a synthesis gas which contains the components $H_2$, CO and $CO_2$ and which is reacted over a catalyst in a synthesis reactor at temperatures from 220° to 300° C. and under a pressure in the range from 20 to 120 bars to produce a product mixture that contains methanol vapor and is withdrawn from the synthesis reactor, the product mixture is cooled to temperatures in the range from 20° to 60° C. to form a condensate which contains water, methanol and methyl formate and to form a gas mixture which contains $H_2$, CO and $CO_2$, the gas mixture is recycled at least in part to the synthesis reactor, and methanol is separated by distillation from the condensate.

That synthesis of methanol is known and has been described, e.g., in Ullmann's Encyclopedia of Industrial Chemistry, 5th Edition (1990). Volume A 16, pages 469 to 475, and in U.S. Pat. Nos. 3,920,717, 3,962,300, and 4,348,486.

It is an object of the invention to improve the utilization of the synthesis gas and to further increase the yield of methanol product.

In the process just described that object is accomplished in accordance with the invention in that a fraction which contains 10 to 100% by weight methyl formate is separated from the condensate which contains water, methanol and methyl formate and said fraction is admixed with the synthesis gas which is fed to the synthesis reactor. As a result, the methyl formate is hydrogenated over the catalyst in the synthesis reactor with hydrogen, which is always present in a surplus, to produce methanol in accordance with the following reaction equation:

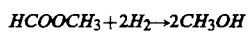

$$HCOOCH_3 + 2H_2 \rightarrow 2CH_3OH$$

The conditions existing in the synthesis reactor result in a substantially complete conversion of the methyl formate to methanol. The methanol synthesis is usually effected over a copper catalyst, which in most cases also contains zinc. However, the process in accordance with the invention is not restricted to the use of a special copper catalyst.

In the distillative after treatment of the product mixture coming from the synthesis reactor the low-boiling components, mainly dimethyl ether, methyl formate and acetone, have previously been separated and used an underfire fuel, e.g., in the production of synthesis gas. In the process in accordance with the invention, care is taken to provide a low-boiling fraction, which comprises 10 to 100% by weight, preferably at least 30% by weight, methyl formate and to recycle such fraction to the methanol synthesis to increase the yield of methanol product. That fraction comprising 10 to 100% by weight methyl formate is separated from the condensate preferably by distillation. That distillative separation is usually effected under a pressure in the range from 1 to 7 bars.

It is recommendable to ensure that the fraction which contains 10 to 100% by weight methyl formate is separated as a liquid from the condensate which contains water, methanol and methyl formate. As a result, that liquid can be pressurized at low cost to the pressure of the synthesis gas by a pump and can be sprayed into the synthesis gas. It will also be desirable to add the methyl formate-containing fraction to the synthesis gas before the synthesis gas is heated to the temperature of 170° to 240° C. at which the synthesis gas enters the synthesis reactor. The fraction which contains methyl formate is heated together with the synthesis gas and thus the synthesis gas is thoroughly mixed with the methyl formate vapor. The boiling point of methyl formate at 1 bar is about 32° C. and at 7 bars is about 97° C.

Further details of the process will be explained with reference to the drawing, which shows a simplified flow scheme.

Synthesis gas is conducted in line 1 to enter the synthesis reactor 2 usually at temperature in the range from 170° to 240°. The synthesis gas contains a surplus of hydrogen and contains the components $H_2$, CO and $CO_2$ in molar concentrations which correspond to the relationship $H_2:(2CO+3CO_2)=1.2$ to 4.0. The reaction in the reactor 2 is effected over a copper catalyst, which is contained, e.g., in tubes, which are cooled in that they are surrounded by boiling water. At temperatures from 220° to 300° C. the pressure at the catalyst is in the range from 20 to 120 bars, preferably from 40 to 100 bars. Instead of a tubular reactor, the reactor may contain the catalyst in one or more fixed beds.

A product mixture which contains methanol vapor and numerous other components, such as unreacted synthesis gas, water vapor and methyl formate, is withdrawn from the reactor 2 in line 3. That product mixture is subjected to a first cooling in a heat exchanger 4 by the cold synthesis gas, which is conducted in line 5. Thereafter the product mixture flows through line 6 to a cooler 7 and flows at temperatures from 20° to 60° C. through line 8 to a separator 9. A gas mixture which contains the synthesis gas components $H_2$, CO and $CO_2$ leaves the separator 9 through line 10. Part of that gas mixture is removed through line 11 from the gas cycle. A compressor 12 compresses the remainder of the gas mixture and forces it into the line 5. Fresh synthesis gas, which has been produced in a plant which is not shown and is known per se, is supplied in line 14.

A condensate which contains water, methanol and methyl formate and other components is withdrawn from the separator 9 and is fed through line 16 to a first distillation column 17. A pressure in the range from 1 to 7 bars is usually maintained in the column 17. Components which have a lower boiling point than methanol and water are withdrawn at the top of the column 17. That fraction is liquid and comprises 10 to 100% by weight methyl formate and is supplied by means of the pump 19 through line 18 to 5 and is sprayed there into the synthesis gas. A methyl formate-containing stream from an extraneous source may also be supplied in line 24 and included in the processing.

A methanol-water mixture is withdrawn through line 20 and is fed to the second distillation column 21, in which the separation is effected. Water is withdrawn in line 22 and methanol in line 23. Water and methanol may be separated in a plurality of stages, as is shown on page 474 in the above-mentioned Ullmann's Encyclopedia of Industrial Chemistry.

EXAMPLE 1

A laboratory apparatus, which corresponds to that shown on the drawing but without the column 21, is operated as follows: A tubular reactor 2, which is cooled by boiling water, contains 100 g of a commercially available Cu-Zn catalyst. A synthesis gas composed of

| | |
|---|---|
| $CO_2$ | 3% by volume |
| CO | 10% by volume |
| $H_2$ | 70% by volume |
| $CH_4 + N_2$ | 17% by volume | is passed at a rate of 900 Nl (Nl=standard liter) per hour through the reactor, which is operated at a temperature of 250° C. and under a pressure of 50 bars. When steady-state conditions have been established, a condensed product which contains 85.94 g methanol and 0.65 g methyl formate is withdrawn from line 16 in a first experimental period of 1 hour. In a second experimental period the condensed product in line 16 is continuously conducted to the middle plate of the distillation column 17, which is operated under atmospheric pressure. The overhead product vapor which is withdrawn from the column 17 at a temperature of 60° C. is condensed by being cooled to 20°. The liquid overhead product contains 30% by weight methyl formate and is added by means of a pump 19 to the synthesis gas in line 1. As a result, the methanol production rate is increased to 86.65 g/h.

EXAMPLE 2

In the same laboratory system as in Example 1, a synthesis gas composed of

| | |
|---|---|
| $CO_2$ | 3% by volume |
| CO | 10% by volume |
| $H_2$ | 75% by volume |
| $CH_4 + N_2$ | 12% by volume | is supplied to the synthesis reactor at a rate of 900 Nl/h. The synthesis of methanol is effected at 80 bars and 250° C. over the same Cu-Zn catalyst as in Example 1. Methyl formate from an extraneous source is admixed at a rate of 10 g/h to the methyl formate-containing overhead product from column 17. The resulting mixture is fed in line 1 together with the synthesis gas to the reactor 2. The use of the methyl formate from an extraneous source results in an increase of the methanol production rate from 113.9 g/h to 120.4 g/h.

It will be understood that the specification and examples are illustrative but not limitative of the present invention and that other embodiments within the spirit and scope of the invention will suggest themselves to those skilled in the art.

We claim:

1. In the catalytic production of methanol from a synthesis gas which contains the components $H_2$, CO and $CO_2$ and which is supplied to are reacted over a catalyst in a synthesis reactor at temperatures from 220° to 300° C. and under a pressure in the range from 20 to 120 bars to produce a product mixture that contains methanol vapor and is withdrawn from the synthesis reactor, the product mixture is cooled to temperatures in the range from 20° to 60° C. to form a condensate which contains water, methanol and methyl formate and to form a gas mixture which contains $H_2$, CO and $CO_2$, the gas mixture is recycled at least in part to the synthesis reactor, and methanol is separated by distillation from the condensate, the improvement which comprises separating from the condensate which contains water, methanol and methyl formate a fraction which comprises 10 to 100% by weight methyl formate, and adding said fraction to the synthesis gas which is supplied to the synthesis reactor.

2. A process according to claim 1, wherein the fraction which comprises 10 to 100% by weight methyl formate is sprayed as a liquid into the synthesis gas.

3. A process according to claim 1, wherein the fraction which comprises 10 to 100% by weight methyl formate is added to the synthesis gas before the synthesis gas is heated to a temperature from 170° to 240° C. at which the synthesis gas enters the synthesis reactor.

4. A process according claim 1, wherein the fraction which comprises methyl formate contains at least 30% by weight methyl formate.

5. A process according to claim 1, wherein the fraction which comprises 10 to 100% by weight methyl formate is separated from the condensate by distillation under a pressure from 1 to 7 bars.

6. A process according to claim 1, wherein a stream which comes from an extraneous source and contains methyl formate is added to the synthesis gas which is supplied to the synthesis reactor.

* * * * *